US012678462B2

(12) United States Patent
Papanikolaou et al.

(10) Patent No.: US 12,678,462 B2
(45) Date of Patent: Jul. 14, 2026

(54) COMBINATION OF COMPOSITIONS FOR ELIMINATION AND ENHANCED ENGRAFTMENT OF HEMATOPOIETIC STEM CELLS IN THE BONE MARROW OF A SUBJECT

(71) Applicant: Miltenyi Biotec B.V. & Co. KG, Bergisch Gladbach (DE)

(72) Inventors: Eleni Papanikolaou, Bergisch Gladbach (DE); Stefan Miltenyi, Bergisch Gladbach (DE); Andreas Bosio, Bergisch Gladbach (DE); Mario Assenmacher, Bergisch Gladbach (DE); Andrew Kaiser, Bergisch Gladbach (DE)

(73) Assignee: Miltenyi Biotec B.V. & Co. KG, Bergisch Gladbach (DE)

( * ) Notice: Subject to any disclaimer, the term of this patent is extended or adjusted under 35 U.S.C. 154(b) by 1085 days.

(21) Appl. No.: 17/424,749

(22) PCT Filed: Jan. 22, 2020

(86) PCT No.: PCT/EP2020/051462
§ 371 (c)(1),
(2) Date: Jul. 21, 2021

(87) PCT Pub. No.: WO2020/152197
PCT Pub. Date: Jul. 30, 2020

(65) Prior Publication Data
US 2022/0133791 A1 May 5, 2022

Related U.S. Application Data

(60) Provisional application No. 62/795,616, filed on Jan. 23, 2019.

(51) Int. Cl.
A61K 35/28 (2015.01)
A61K 40/11 (2025.01)
A61K 40/31 (2025.01)
A61K 40/42 (2025.01)

(52) U.S. Cl.
CPC .............. *A61K 35/28* (2013.01); *A61K 40/11* (2025.01); *A61K 40/31* (2025.01); *A61K 40/4221* (2025.01); *A61K 2239/31* (2023.05); *A61K 2239/38* (2023.05); *A61K 2239/48* (2023.05)

(58) Field of Classification Search
None
See application file for complete search history.

(56) References Cited

U.S. PATENT DOCUMENTS

| | | | | |
|---|---|---|---|---|
| 6,030,836 | A | * 2/2000 | Thiede | C12N 5/0647 435/455 |
| 9,233,125 | B2 | 1/2016 | Davila et al. | |
| 2016/0144026 | A1* | 5/2016 | Lutteropp | A61P 35/00 424/134.1 |
| 2018/0355052 | A1 | 12/2018 | Orentas et al. | |

FOREIGN PATENT DOCUMENTS

| | | |
|---|---|---|
| CN | 106103490 A | 11/2016 |
| CN | 108884440 A | 11/2018 |
| WO | WO 2015/075469 | 5/2015 |
| WO | WO 2015/075470 | 5/2015 |
| WO | WO 2015/142314 | 9/2015 |
| WO | WO 2016/055551 | 4/2016 |
| WO | WO 2016/097231 | 6/2016 |
| WO | WO 2016/193696 | 12/2016 |
| WO | WO 2017/058753 | 4/2017 |
| WO | WO 2017/068361 | 4/2017 |
| WO | WO 2017/079744 | 5/2017 |
| WO | WO 2017/091546 | 6/2017 |
| WO | WO 2014/127261 | 8/2017 |
| WO | WO 2018/061012 | 4/2018 |
| WO | WO 2019/162695 | 8/2019 |

OTHER PUBLICATIONS

O'Hear et al., haematologica, 2015; 100(3): 336-344 (Year: 2015).*
Patel et al., eJHaem. 2022; 3(Suppl. 1): 24-31 (Year: 2022).*
Pulsipher et al., Blood. 2009; 114: 2606-2616 (Year: 2009).*
Heideveld et al., haematologica, 2015; 100(11) (Year: 2015).*
Luigi Naldini, EMBO Mol Med (2019) 11: e9958 (Year: 2019).*
Urbanska et al., Cancer Res; 2012, 72(7): 1844-1852 (Year: 2012).*
Fricke et al., PLoS ONE 4(7): e6157. doi: 10.1371/journal.pone. 0006157 (Year: 2009).*
Dunbar et al., Science (2018) 359, 175 (Year: 2018).*
Tamada et al., Clin Cancer Res; 18(23); 6436-45 (Year: 2012).*
Abbuehl et al., "Long-Term Engraftment of Primary Bone Marrow Stromal Cells Repairs Niche Damage and Improves Hematopoietic Stem Cell Transplantation," Cell Stem Cell, Aug. 2017, 21:241-255, 22 pages.
Anderson et al., "In vitro evaluation of hematopoiesis in mice treated with busulphan or nitrogen mustard," Biomed., Jan. 1982, 36:149-152.

(Continued)

*Primary Examiner* — Christina M Borgeest
(74) *Attorney, Agent, or Firm* — Fish & Richardson P.C.

(57) ABSTRACT

The present invention provides a combination of compositions comprising i) a composition comprising I) a population of T cells, NK cells or cytotoxic immune effector cells comprising a chimeric antigen receptor specific for a stem cell antigen and/or, II) α) a population of T cells, NK cells or cytotoxic immune effector cells comprising a chimeric antigen receptor specific for a tag of a tagged polypeptide, wherein said tagged polypeptide binds specifically to a stem cell antigen, and β) said tagged polypeptide, and ii) a composition comprising a) a population of CD34+ hematopoietic stem cells, and b) one or more accessory or contributory cell populations selected from the group consisting of myeloid cell lineages expressing CD14, CD11b, CD11c, CD123, CD33; CD36; CD47, CD66b, CD235a, CD146 and CD326. A method applying these compositions to a subject in need thereof are also provided.

5 Claims, 6 Drawing Sheets

(56)                    References Cited

OTHER PUBLICATIONS

Arai et al., "Myeloid Conditioning with c-kit-Targeted CAR-T Cells Enables Donor Stem Cell Engraftment," Mol. Ther., May 2018, 26(5):1181-1197, 25 pages.
CAS-No. 89889-52-1, "Biotinamidohexanoyl-6-aminohexanoic acid N-hydroxysuccinimide ester," Sigma-Aldrich, retrieved on Feb. 11, 2022, retrieved from URL <https://www.sigmaaldrich.com/US/en/product/sigma/b3295?context-bbe>, 7 pages.
Chhabra et al., "Hematopoietic stem cell transplantation in immunocompetent hosts without radiation or chemotherapy," Sci. Transl. Med., Aug. 2016, 8(351):1-11.
Choi et al., "Murine male germ cell apoptosis induced by busulfan treatment correlates with loss of c-kit-expression in a Fas/FasL- and p53-independent manner," FEBS Letters, Aug. 2004, 575:41-51.
Czechowicz et al., "Efficient Transplantation via Antibody-Based Clearance of Hematopoietic Stem Cell Niches," Nov. 2007, 318:1296-1299, 5 pages.
Down et al., "Late Tissue-Specific of Total Body Irradiation and Busulfan in a Murine Bone Marrow Transplant Model," Int. J. Radiat. Oncol. Biol, Biol., Phys., Jul. 1989, 17(1):109-116.
Goncalves et al., "MGTA-145 in Combination with Plerixafor Rapidly Mobilizes High Numbers of Hematopoietic Stem Cells and Graft-Versus-Host Disease Inhibiting Myeloid-Derived Suppressor Cells in Non-Human Primates," Blood, Nov. 2018, 132(Supplement 1):116, 4 pages (abstract).
Guest et al., "Drugs toxic to the bone marrow that target the stromal cells," Immunopharmacology, 2000, 46: 103-112.

Hays et al., "'Stromal' and hemopoietic stem cell abnormalities in long-term cultures of marrow from busulfan-treated mice," Exp. Hematol., Apr. 1982, 10(4):383-392.
Huang et al., "Targeting CD47: the achievements and concerns of current studies on cancer immunotherapy," J. Thorac. Dis., Feb. 2017, 9(2):E168-E174.
International Preliminary Report on Patentability in International Appln. No. PCT/EP2020/051462, dated Jul. 27, 2021, 8 Pages.
International Search Report and Written Opinion in International Appln. No PCT/EP2020/051462, dated Apr. 3, 2020, 10 pages.
Liu et al., "Use of chimeric antigen hematopoietic stem cell transplantation," Immunotherapy, Jan. 2019, 11(1): 37-44.
Palchaudhuri et al., "Non-genotoxic conditioning for hematopoietic stem cell transplantation using a hematopoietic-cell-specific internalizing immunotoxin," Nat. Biotechnol., Jun. 2016, 34:738-745, 10 pages.
Tanaka et al., "Oncostatin M, a multifunctional cytokine," Rev. Physiol. Biochem. Pharmacol., Jun. 2003, 149:39-52.
Wathen et al., "Residual injury to the hemopoietic microenvironment following sequential radiation and busulfan," Int. J. Radiation Oncology Biol. Phys., Aug. 1982, 8(8):1315-1322.
Wulf et al., "Anti-CD45-mediated cytoreduction to facilitate allogeneic stem cell transplantation," Blood, Mar. 2003, 101(6):2434-2439.
Xaymardan et al., "Bone Marrow Stem Cells: Properties and Pluripotency," Principles of Regenerative Medicine, 1st ed., 2008, Chapter 16, 268-283.
Xue et al., "Antibody targeting KIT as pretransplantation conditioning in immunocompetent mice," Blood, Dec. 2010, 116(24):5419-5422, 5 pages.
Zhao et al., "Universal CARs, universal T cells, and universal Car T cells," J. Hematol. Oncol., Nov. 2018, 11(132):1-9.

* cited by examiner

COMBINATION OF COMPOSITIONS FOR ELIMINATION AND ENHANCED ENGRAFTMENT OF HEMATOPOIETIC STEM CELLS IN THE BONE MARROW OF A SUBJECT

CLAIM OF PRIORITY

This application is a § 371 National Stage Application of PCT/EP2020/051462, filed Jan. 22, 2020, which claims priority to U.S. Patent Application Ser. No. 62/795,616, filed on Jan. 23, 2019, the entire contents of which are hereby incorporated by reference.

BACKGROUND

Hematopoietic stem cell (HSC) transplantation has been used to treat malignant hematologic diseases for over 50 years. Recipients of allogeneic hematopoietic stem cell transplants must receive a so-called "conditioning" prior to transplantation in order to attenuate their own hematopoiesis, so that donor hematopoietic cells can engraft, i.e. migrate to the recipient's bone marrow (BM) and proliferate. Conditioning regimens for allogeneic transplantation usually consist of both myeloablative and lymphoablative regimens aiming to reduce the burden of the disease by eradicating malignant cells and simultaneously to immunosuppress the recipient's lymphoid cells, to allow robust and sustained donor hematopoietic stem cell engraftment. The clinical standard of care are alkylators and lymphodepleting agents and the process typically includes high-dose chemotherapy, in combination with whole-body irradiation, that induces very high stem cell and immune cell toxicity. Such regimens are associated with substantial risk of morbidity and mortality for patients and increased toxicity to non-hematopoietic tissues. Busulfan (BU), a sulfonic acid ester (alkylating agent) used for the treatment of chronic myelogenous leukemia and as a conditioning drug in pediatric bone marrow transplantation, also causes permanent damage to bone marrow stromal cells (Guest and Uetrecht: Drugs toxic to the bone marrow that target the stromal cells, Immunopharmacology 46; 2000 103-112). This inhibition of stromal cell function was also observed by others (Anderson et al., 1982; Hays et al., 1982; Wathen et al., 1982) and manifested a significantly diminished ability of murine stroma to support hematopoiesis and to produce CFU-F and CFU-GM. The role of this incomplete recovery of the stromal cells in BU-induced bone marrow hypoplasia and the nature of the lesions remain unknown, but it is clear that BU has a profound effect on the stromal layer, resulting in long-term compromised ability of stromal cells to reproduce and to support normal hematopoiesis. In subsequent experiments, BU administration to mice caused cataract formation and hair greying suggesting that other cell renewal systems were also affected (Down et al, Late tissue-specific toxicity of total body irradiation and busulfan in a murine bone marrow transplant model, Int J Radiat Oncol Biol Phys. 1989 July; 17(1):109-16). Later studies confirmed that BU also inhibits the of SDF-1 (stromal derived factor or CXCL12) and SCF (stem cell factor). SDF-1 and SCF are produced by bone marrow stromal cells and their function is to promote homing and engraftment of HSCs within the recipient bone marrow (Xaymardan, Cimini, Weisel, Li: in Bone Marrow Stem Cells: Properties and Pluripotency, Editors: Atala, Lanza, Thomson, Nerem, Principles of Regenerative Medicine, Academic Press, 2008, p 268-283, ISBN 9780123694102 and Choi et al, murine male germ cell apoptosis induced by busulfan treatment correlates with loss of c-kit-expression in a Fas/FasL- and p53-independent manner FEBS Lett. 2004 Sep. 24; 575(1-3):41-51).

Hence, busulfan causes toxicity also to non-hematopoietic tissues, namely the stromal cells of the bone marrow and thus it can significantly impair the establishment of new hemopoiesis upon allogeneic or autologous HSC transplantation.

With the emergence of gene therapy strategies, reduced toxicity conditioning regimens are mandatory as gene therapy is mainly directed towards treating patients suffering from monogenic diseases and not malignant diseases. In that scenario, it is acceptable to administer chemotherapy when the underlying disease is malignant, but it is highly undesirable in a non-malignant monogenic disease background, such as aplastic anemias, primary immunodeficiencies and hemoglobinopathies. Moreover, such conditioning is completely intolerable in patients with defects in DNA repair who are prone to hematopoietic malignancies, such as ataxia telangiectasia, Bloom syndrome, and Fanconi anemia. Therefore, the need to develop novel methods for promoting patients' survival and for circumventing the toxicity to other cells or tissues during conditioning is imperative. Thus, new targeted space-making agents that will ultimately substitute alkylating agents and spare non-hematopoietic tissues from acute toxicity, are currently being evaluated. To this end, promising results have been observed in humans using antibody-based approaches including anti-c-kit (CD117) (Czechowicz, et al, 2007 Efficient transplantation via antibody-based clearance of hematopoietic stem cell niches. Science 318: 1296-1299 and Xue, et al, 2010. Antibody targeting KIT as pre transplantation conditioning in immunocompetent mice. Blood 116: 5419-5422) or anti-CD45 antibodies which directly target HSCs (Wulf et al, 2003, Anti-CD45-mediated cytoreduction to facilitate allogeneic stem cell transplantation. Blood 101: 2434-2439). Results with anti-c-kit antibody were enhanced by combination with anti-CD47 antibody (Chhabra et al. 2016, Hematopoietic stem cell transplantation in immunocompetent hosts without radiation or chemotherapy. Sci Transl Med 8: 351ra105) and those with anti-CD45 antibody were greatly enhanced by conjugation to saporin (Palchaudhuri et al, Non-genotoxic conditioning for hematopoietic stem cell transplantation using a hematopoietic-cell-specific internalizing immunotoxin. Nat Biotechnol. 2016 July; 34:738-45).

There is a need in the art for improved or alternative methods and/or compositions for elimination and enhanced engraftment of hematopoietic stem cells in the bone marrow of a subject.

SUMMARY OF THE INVENTION

The current invention discloses methods of generating an immunocompetent and higher survival donor graft in combination with a superior bone marrow conditioning strategy of the recipient that preserves the function of the recipient's bone marrow stromal cells and supports/enhances attachment and survival of the donor's hemopoietic cells.

The invention provides two components (compositions): The first component is related to the status of the bone marrow of the recipient and the second compound is related to the status of the graft provided by the donor. In gene therapy (autologous transplantation of genetically corrected cells) the donor and the recipient are the same.

The first component is a system that comprises pharmaceutical agents for use in immunotherapy and/or hematopoietic stem cell transplantation for reducing the side effects of chemotherapy and circumventing the toxicity of an antigen-recognizing receptor against antigen expressing non-target and target cells in an individual. The system includes an antigen-recognizing receptor that specifically recognizes a moiety (tag) bound to a polypeptide; then the polypeptide recognizes specific types of target cells (antigens/markers on the target cells) such as hematopoietic cells in the individual. The antigen-recognizing receptor is exemplified by chimeric antigen receptors (CAR) expressed on the surface of an immune effector cell. In some embodiments of the invention, in order to mediate the recognition and binding between CAR-T cells and the target cells, an adapter molecule is required. A universal CAR T cell adapter molecule is composed e.g. of an antibody or antigen binding fragment thereof (e.g. Fab) specific to recognize an antigen/marker on the target cells plus a secondary moiety (a tag) which is recognized only by the CAR-T cells. This way, the adapter molecule serves as a recognition bridge between the target cells and the CAR-T cells. By using antibodies and Fabs different cell populations can be targeted and the CAR-T cells are only functional in the presence of the adapter molecule. The system also includes hematopoietic cells and non-hematopoietic stromal cells of the bone marrow resistant to recognition of the same antigen by the antigen-recognizing receptor. Here, we explore a related, but distinct, approach using chimeric antigen receptor T (CAR-T) cells to remove HSCs in bone marrow (BM), aiming to provide proof-of-concept that CAR-T cells which carry a chimeric receptor that recognizes e.g. biotin, can target specified cell populations when combined with a certain biotinylated antibody of choice. This way one can achieve removal of this cell population and reach effective BM conditioning without affecting stromal cells. For example, one could utilize a chimeric antigen receptor which in essence e.g. has a biotin-specific antibody as the extracellular component of the CAR, combined with a biotinylated CDx (CDx may be e.g. c-Kit, CD33, CD34, CD38, CD45RA, CD71, CD90, CD131, CD133, or CD135) antibody or antigen binding fragment thereof that recognizes the specific cell population, i.e. c-Kit expressing cells, and/or CD34+, and/or CD33+, and/or CD38+, and/or CD45RA+, and/or CD71+, and/or CD90+, and/or CD131+, and/or CD133+, and/or CD135+ cells. This strategy also provides transient CAR-T activity as the CAR-T cells will be active only in the presence of the adapter molecule, conferring thus the possibility to timely regulate the CAR-T activity. This part of the system is intended to specifically eliminate hematopoietic stem cells in the bone marrow and leave unaffected the bone marrow's stromal cells.

The second component, accordingly, comprises methods and compositions for generating a potent cell graft with enhanced homing and attachment to a target tissue of a subject, such as the bone marrow niche. In certain aspects, such methods and compositions relate to or comprise the identification of other accessory cells that promote HSC and progenitor stem cell retention in one or more target tissues of a subject (e.g., the bone marrow stem cell niche). The methods and compositions disclosed herein are useful for promoting HSC retention in one or more target tissues, as well as enhancing the engraftment efficiency of transplanted stem cells (e.g., HSCs) in a target tissue of a subject. In some embodiment the transplanted stem cells may be genetically modified as disclosed herein. In certain embodiments, disclosed herein are methods of increasing stem cell engraftment efficiency in a target tissue of a subject, the method comprising administering a cell graft consisting of c-Kit expressing cells, and/or CD34+, and/or CD33+, and/or CD38+, and/or CD45RA+, and/or CD71+, and/or CD90+, and/or CD131+, and/or CD133+, and/or CD135+ hemopoietic stem cells and other accessory or contributory cell populations that enhance the attachment of the donor's hemopoietic stem cells to the recipient's bone marrow. Such contributory cells can be any of the following myeloid lineages: CD14, CD11b, CD11c, CD123, CD33, CD36, CD47, CD66b, CD235a, CD146 and/or CD326; i.e. at least one of said antigens or any combination thereof. In one embodiment of the invention, the graft does not comprise any of the following lymphoid cell populations, so called inhibitory cell populations, namely CD3, CD19 and CD56 expressing cells. In another embodiment of the invention the graft also comprises so called inhibitory cell populations, namely CD3, CD19 and CD56 expressing cells.

The rationale of combining hematopoietic stem cells as disclosed herein with any of the contributory cells is based on the following:

1. A certain cell population, called CD34dim cells, was found to be enriched in myeloid-derived suppressor sells such as monocytes or other myeloid cells (e.g. CD11b and CD14) that inhibited graft-versus-host disease in non-human primates: Goncalves et al. "MGTA-145 in combination with plerixafor rapidly mobilizes high numbers of hematopoietic stem cells and graft-versus-host disease inhibiting myeloid-derived suppressor cells in non-human primates" (Blood 132 (Suppl 1), page 116.

2. Macrophages in the MS-5 co-culture system secreted factors that supported the stem cell niche: In particular, media containing secretions from macrophages was collected and then cultured together with SDF-1 producing stromal cells to see if SDF-1 production was stimulated by anything in the media, such as oncostatin M. Oncostatin M is a 28 kDa multifunctional member of the IL-6 family of cytokines that is secreted by monocytes, macrophages, neutrophils and activated T-lymphocytes (Tanaka, et al, Rev Physiol Biochem Pharmacol 2003, 149: 39-533) (WO 2017/079744 A1).

3. Combining CD34 and CD46 positive cells. CD47, also named integrin-associated protein (IAP), is a widely expressed trans-membrane glycoprotein. It provides a "do not eat" signal by binding to the N-terminus of signal regulatory protein alpha (SIRPα) on immune cells and suppresses phagocytosis. Hematopoietic stem cells transiently up-regulate CD47 expression to escape phagocytosis by macrophages before and during mobilization (Yuting et al, Targeting CD47: the achievements and concerns of current studies on cancer immunotherapy, J Thorac Dis. 2017 February; 9(2): E168-E174).

The system has to work with both components, i.e. maintaining both bone marrow stromal cells viability as well as augmenting the engraftment potential of the donor's cells. BM stromal cell viability is mandatory because otherwise, molecules that induce production of engraftment molecules such as SDF-1 will not be produced from harmed stromal cells.

The present invention relates to the treatment of diseases such as:

Cancer, Aplastic anemia, Fanconi anemia, Diamond-blackfan syndrome, Sickle cell disease, Thalassemia, Paroxysmal nocturnal hemoglobinuria, Chediak-Higashi syndrome, Chronic granulomatous disease, Glanzmann thrombasthenia, Osteopetrosis, Lysosomal storage disorders, Gaucher disease, Niemann-Pick, Mucopolysaccharidosis, Glycoproteinoses, Immune deficiencies, Ataxia telangiectasia, DiGeorge syndrome, Severe combined immunodeficiency (SCID), Wiscott-Aldrich, Kostmann syndrome, Shwachman-Diamond syndrome.

BRIEF DESCRIPTION OF THE DRAWINGS

(FIG. 6A)

NSG mice were engrafted with CD20+tumor cells (Raji, expressing firefly luciferase) on day-5, CAR T cells were infused on day 0, adapter molecules (50 µg/mouse) were administered by i.p. injection on a daily basis. (FIG. 6B) Tumor progression (median of groups with n=5 mice) was monitored by bioluminescence imaging (IVIS). Control of tumor growth was only observed in the mice receiving both CAR T cells and adapter molecules and the CD20 direct CAR positive control.

DETAILED DESCRIPTION OF THE INVENTION

Figure 1:
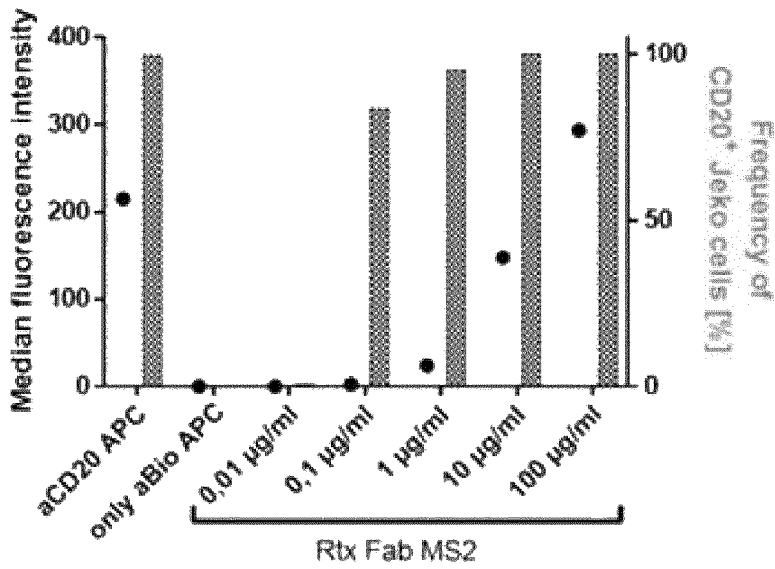
FIG. 1. Titration of Biotin-crosslinker Y conjugated to CD20 (Rtx Fab) on CD20$^+$ Jeko-1 target cells. Different concentrations of FAb (0.01-100 µg/ml) was added to 50.000 target cells in 50 µl and secondary staining was performed with anti-Biotin APC (Miltenyi Biotec). In a control sample direct anti-CD20 staining was performed using an anti-CD20-APC conjugate (Miltenyi Biotec).

In one aspect, the present invention provides a combination of compositions comprising
  i) a composition comprising
  I) a population of T cells, NK cells or cytotoxic immune effector cells comprising a chimeric antigen receptor specific for a stem cell antigen and/or,
  II) α) a population of T cells, NK cells or cytotoxic immune effector cells comprising a chimeric antigen receptor specific for a tag of a tagged polypeptide, wherein said tagged polypeptide binds specifically to a stem cell antigen, and
  β) said tagged polypeptide, and
  ii) a composition comprising
  a) a population of CD34+ hematopoietic stem cells, and
  b) one or more accessory or contributory cell populations selected from the group consisting of myeloid cell lineages expressing one or more (at least one) of the markers (antigens) CD14, CD11b, CD11c, CD123, CD33; CD36; CD47, CD66b, CD235a, CD146 and CD326.

In one embodiment of the invention, said stem cell antigen may be a hematopoietic stem cell antigen.

Said combination of compositions for use in treatment of a subject. Said subject may suffer from a disease as disclosed herein. Said treatment may be the elimination and (subsequent) enhanced engraftment of hematopoietic stem cells in the bone marrow of said subject.

Said combination of compositions for use in the elimination and the (subsequent) enhanced engraftment of hematopoietic stem cells in the bone marrow of a subject. Said subject may suffer from a disease as disclosed herein.

Said subject may provide T cells, NK cells or cytotoxic immune effector cells that may be genetically modified in-vitro to said T cells, NK cells or cytotoxic immune effector cells comprising a chimeric antigen receptor of composition i), and said subject may provide the CD34+ hematopoietic stem cells of composition ii) part a) and may provide said one or more accessory or contributory cell populations (part b).

In one embodiment of the invention, said one or more accessory or contributory cell populations may comprise T cells and/or B cells and/or NK cells.

Alternatively, said one or more accessory or contributory cell populations may comprise T cells and/or B cells and/or NK cells but in a lower concentration due to in-vitro (at least partial) depletion of T cells and/or B cells and/or NK cells by using e.g. anti-CD3, anti-CD19 and/or anti-CD56 antibodies or antigen binding fragments thereof from a sample provided by said subject that comprises accessory and contributory cell populations and T cell, B cells and NK cells, as compared to a non-depleted sample provided by said subject that comprises accessory and contributory cell populations and T cell, B cells and NK cells.

Alternatively, said one or more accessory or contributory cell populations do not comprise T cells and/or B cells and/or NK cells.

Said composition i) may be applied to a subject in need thereof to eliminate the subject's hematopoietic stem cells. This procedure may also be referred to as myeloablation.

Subsequently, said composition ii) may be applied to said subject. This procedure leads to an engraftment of hematopoietic stem cells in the bone marrow of said subject.

The composition ii) may comprise
a) a population of CD34+ hematopoietic stem cells,
b) a population of CD14+ hematopoietic cells, and optionally
c) one or more accessory or contributory cell populations selected from the group consisting of myeloid cell lineages expressing one or more of the markers CD11b, CD11c, CD123, CD33; CD36; CD47, CD66b, CD235a, CD146 and CD326.

The composition of i) may also comprise two or more antigen binding domains specific for stem cell antigens or two or more tags specific for tags of tagged polypeptides that are specific for stem cell antigens.

Said combination of compositions, wherein said stem cell antigen is c-Kit, and/or CD34, and/or CD33, and/or CD38, and/or CD45RA, and/or CD71, and/or CD90, and/or CD131, and/or CD133, and/or CD135.

Said combination of compositions, wherein said stem cell antigen preferentially is c-Kit, CD33, CD34, CD133, CD90, CD71, or any combination thereof.

Said combination of compositions, wherein said CD34+ hematopoietic stem cells are genetically engineered.

Said combination of compositions, wherein said CD34+ hematopoietic stem cells are genetically engineered to correct a deficient monogenetic gene or cancerous gene that is inherent to the subject to be treated to a healthy variant of said monogenetic gene or cancerous gene. Deficient monogenetic gene for example is the gene encoding the beta chain of hemoglobin in the case of thalassemia and sickle cell disease.

Said genetically engineered CD34+ hematopoietic stem cells may be autologous CD34+ hematopoietic stem cells or allogenic CD34+ hematopoietic stem cells of the subject to be treated.

Said combination of compositions, wherein said CD34+ hematopoietic stem cells are not genetically engineered (naturally CD34+ hematopoietic stem cells). Said naturally CD34+ hematopoietic stem cells may be autologous CD34+ hematopoietic stem cells or allogenic CD34+ hematopoietic stem cells of the subject to be treated.

Said combination of compositions, wherein said one or more accessory or contributory cell populations express one or more of the markers selected from the group consisting of CD14, CD11b, CD11c, CD123, CD33, CD36, CD47, CD66b, CD235a, CD146 and CD326. Said cell populations may express a single of these markers or several of these markers in any combination of said markers such as CD34+ and CD90+ cells (as stem cells) combined with primarily CD14, and any other of the following markers, i.e. CD11b, CD11c, CD123, CD33, CD36, CD47, CD66b, CD235a, CD146 and CD326.

Said combination of compositions, wherein said genetically engineered CD34+ hematopoietic stem cells are cells that have been corrected with regard to a disease.

Said disease may be a disease which can be cured by transplantation of CD34+ cells.

Said disease may be a genetic disease, preferentially a monogenetic disease or a cancer.

Said combination of compositions, wherein said population of T cells, NK cells or cytotoxic immune effector cells comprising a chimeric antigen receptor and said population of CD34+ hematopoietic stem cells and said one or more accessory or contributory cell populations are autologous cells with regard to a subject that receives the cells in a treatment of said disease.

Said combination of compositions for use in treatment of a disease in a subject suffering from said disease.

Said diseases may be selected from the group consisting of Cancer, Aplastic anemia, Fanconi anemia, Diamond-blackfan syndrome, Sickle cell disease, Thalassemia, Paroxysmal nocturnal hemoglobinuria, Chediak-Higashi syndrome, Chronic granulomatous disease, Glanzmann thrombasthenia, Osteopetrosis, Lysosomal storage disorders, Gaucher disease, Niemann-Pick, Mucopolysaccharidosis, Glycoproteinases, Immune deficiencies, Ataxia telangiectasia, DiGeorge syndrome, Severe combined immunodeficiency (SCID), Wiscott-Aldrich, Kostmann syndrome, and Shwachman-Diamond syndrome.

Often (and normally) the hematopoietic stem cells to be eliminated are not diseased cells. But in some cases, the hematopoietic stem cells are themselves diseased cells, e.g. in the context of Fanconi anemia, ataxia telangiectasia and Bloom syndrome.

Said combination of compositions may also comprise a AND NOT CAR approach, i.e. said T cells, NK cells or cytotoxic immune effector cells may comprise a second CAR (in addition to above-described first CAR), which is an inhibitory CAR (iCAR), and wherein said antigen binding domain is specific for an antigen that is not expressed on the target cell to that the first CAR is directed to.

As disclosed e.g. in WO2018061012A1, instead of an activating domain (such as FcRy or CD3-ζ) of a CAR, an iCAR may possess a signaling domain derived from an inhibitory receptor which can antagonize T cell activation, such as CTLA-4, PD-1 or an NK inhibitory receptor.

Therefore, the iCAR (the second CAR that binds to the second antigen) may comprise a cytoplasmic signaling domain comprising an inhibitory domain, wherein said inhibitory domain may be a signal transduction element of an immune checkpoint protein.

In an embodiment of the invention, said immune cell may comprise said first CAR and said second CAR, wherein said first CAR may comprise a spacer between the antigen binding domain and the transmembrane domain and wherein said second CAR may comprise a spacer between the antigen binding domain and the transmembrane domain.

The spacer of the first CAR may be different to the spacer of the second CAR. This may prevent formation of heterodimers of the first CAR and the second CAR.

The spacer of the first CAR may have a different length and/or size and/or configuration from the spacer of the second CAR.

But the spacer of the first CAR and the spacer of the second CAR may be sufficiently similar to result in a co-localization of the first CAR and the second CAR following binding of the first antigen and second antigen, respectively.

In another aspect, the present invention also provides a method for eliminating hematopoietic stem cells in the bone marrow of a subject suffering from a disease and increasing engraftment efficiency of a population of CD34+ hematopoietic stem cells, the method comprising administering to said subject i) a composition comprising I) a population of T cells, NK cells or cytotoxic immune effector cells comprising a chimeric antigen receptor specific for a stem cell antigen or, II) α) a population of T cells, NK cells or cytotoxic immune effector cells comprising a chimeric antigen receptor specific for a tag of a tagged polypeptide, wherein said tagged polypeptide binds specifically to a stem cell antigen, and β) said tagged polypeptide, thereby specifically eliminating said hematopoietic stem cells in the bone marrow of the subject and leaving unaffected the bone marrow's stromal cells, and ii) a composition comprising a) a population of CD34+ hematopoietic stem cells, b) one or more accessory or contributory cell populations selected from the group consisting of myeloid cell lineages expressing one or more of the markers CD14, CD11b, CD11c, CD123, CD33; CD36; CD47, CD66b, CD235a, CD146 and CD326, thereby increasing the stem cell engraftment efficiency into the bone marrow of the subject.

Said population of T cells, NK cells or cytotoxic immune effector cells comprising a chimeric antigen receptor specific for said tag of said tagged polypeptide may be applied to said subject simultaneously, before or after the application of said tagged polypeptide to said subject. Said composition i) may be applied, before application of the composition ii) to the subject. The composition i) and/or the composition ii) may be applied once or more than once to the subject. The use of the adapterCAR system may be preferred in the method as disclosed herein. In that scenario, the adapter-CAR immune cells, e.g. adapter CAR-T cells will attack the CD34 cells only during the presence of the tagged (e.g. biotinylated) anti CD34 antibody. Once the antibody is cleared (by kidneys) from the organism, the adapter CAR-immune cells will still circulate in the blood stream but cannot attack the new CD34+ cells.

Said method, wherein said population of 34+ hematopoietic stem cells are genetically engineered cells or healthy cells.

Said method, wherein said population of CD34+ hematopoietic stem cells are autologous cells or allogenic cells of subject.

Said subject may be a human.

It is also an aspect of the present invention that the two compositions of the combination of compositions as disclosed herein may be used independently.

Then in a preferred embodiment a composition comprising i)) a population of T cells, NK cells or cytotoxic immune effector cells comprising a chimeric antigen receptor specific for a tag of a tagged polypeptide, wherein said tagged polypeptide binds specifically to a stem cell antigen, and ii) said tagged polypeptide, may be used for myeloablation in a subject.

In another embodiment of the present invention a composition comprising a) a population of CD34+ hematopoietic stem cells, and b) one or more accessory or contributory cell populations selected from the group consisting of myeloid cell lineages expressing one or more of the markers CD14, CD11b, CD11c, CD123, CD33; CD36; CD47, CD66b, CD235a, CD146 and CD326, may be used for enhanced engraftment in the bone marrow of the subject.

In another embodiment of the present invention a composition comprising a) a population of CD34+ hematopoietic stem cells, b) a population of CD14+ hematopoietic cells, and optionally c) one or more accessory or contributory cell populations selected from the group consisting of myeloid cell lineages expressing one or more of the markers CD11b, CD11c, CD123, CD33; CD36; CD47, CD66b, CD235a, CD146 and CD326, may be used for enhanced engraftment in the bone marrow of the subject.

All definitions, characteristics and embodiments defined herein with regard to an aspect of the invention, e.g. the first aspect of the invention, also apply mutatis mutandis in the context of the other aspects of the invention as disclosed herein.

Definitions

Unless defined otherwise, technical and scientific terms used herein have the same meaning as commonly understood by one of ordinary skill in the art to which this invention belongs.

As used herein the term "comprising" or "comprises" is used in reference to compositions, methods, and respective component(s) thereof, that are essential to the method or composition, yet open to the inclusion of unspecified elements, whether essential or not.

In general, a CAR may comprise an extracellular domain (extracellular part) comprising the antigen binding domain, a transmembrane domain and a cytoplasmic signaling domain (intracellular signaling domain). The extracellular domain may be linked to the transmembrane domain by a linker or spacer. The extracellular domain may also comprise a signal peptide. In some embodiments of the invention the antigen binding domain of a CAR binds a tag or hapten that is coupled to a polypeptide ("haptenylated" or "tagged" polypeptide), wherein the polypeptide may bind to an antigen expressed on a target cell such as a (hematopoietic) stem cell as disclosed herein, or a disease-associated antigen such as a tumor associated antigen (TAA) that may be expressed on the surface of a target cell such as a cancer cell.

Such a CAR may be referred to as "anti-tag" CAR or "adapterCAR" or "universal CAR" as disclosed e.g. in U.S. Pat. No. 9,233,125B2.

The haptens or tags may be coupled directly or indirectly to a polypeptide (the tagged polypeptide), wherein the polypeptide may bind to said target cell such as a (hematopoietic) stem cell, or disease associated antigen expressed on the (cell) surface of a target. The tag may be e.g. dextran or a hapten such as biotin or fluorescein isothiocyanate (FITC) or phycoerythrin (PE) or thiamin, but the tag may also be a peptide sequence e.g. chemically or recombinantly coupled to the polypeptide part of the tagged polypeptide. The tag may also be streptavidin. The tag portion of the tagged polypeptide is only constrained by being a molecular that can be recognized and specifically bound by the antigen binding domain specific for the tag of the CAR. For example, when the tag is FITC (Fluorescein isothiocyanate), the tag-binding domain may constitute an anti-FITC scFv. Alternatively, when the tag is biotin or PE (phycoerythrin), the tag-binding domain may constitute an anti-biotin scFv or an anti-PE scFv, respectively.

A "signal peptide" refers to a peptide sequence that directs the transport and localization of the protein within a cell, e.g. to a certain cell organelle (such as the endoplasmic reticulum) and/or the cell surface.

Generally, an "antigen binding domain" refers to the region of the CAR that specifically binds to an antigen, e.g. to an antigen expressed on a (hematopoietic) stem cell, to a tumor associated antigen (TAA) or tumor specific antigen (TSA). The CARs of the invention may comprise one or more antigen binding domains (e.g. a tandem CAR). Generally, the targeting regions on the CAR are extracellular. The antigen binding domain may comprise an antibody or an antigen binding fragment thereof. The antigen binding domain may comprise, for example, full length heavy chain, Fab fragments, single chain Fv (scFv) fragments, divalent single chain antibodies or diabodies. Any molecule that binds specifically to a given antigen such as affibodies or ligand binding domains from naturally occurring receptors may be used as an antigen binding domain Often the antigen binding domain is a scFv. Normally, in a scFv the variable regions of an immunoglobulin heavy chain and light chain are fused by a flexible linker to form a scFv. Such a linker may be for example the "$(G_4/S)_3$-linker".

In some instances, it is beneficial for the antigen binding domain to be derived from the same species in which the CAR will be used in. For example, when it is planned to use it therapeutically in humans, it may be beneficial for the antigen binding domain of the CAR to comprise a human or humanized antibody or antigen binding fragment thereof. Human or humanized antibodies or antigen binding fragments thereof can be made by a variety of methods well known in the art.

"Spacer" or "hinge" as used herein refers to the hydrophilic region which is between the antigen binding domain and the transmembrane domain. The CARs of the invention may comprise an extracellular spacer domain but is it also possible to leave out such a spacer. The spacer may include e.g. Fc fragments of antibodies or fragments thereof, hinge regions of antibodies or fragments thereof, CH2 or CH3 regions of antibodies, accessory proteins, artificial spacer sequences or combinations thereof. A prominent example of a spacer is the CD8alpha hinge.

The transmembrane domain of the CAR may be derived from any desired natural or synthetic source for such domain. When the source is natural the domain may be derived from any membrane-bound or transmembrane protein. The transmembrane domain may be derived for example from CD8alpha or CD28. When the key signaling and antigen recognition modules (domains) are on two (or even more) polypeptides then the CAR may have two (or more) transmembrane domains. The splitting key signaling and antigen recognition modules enable for a small molecule-dependent, titratable and reversible control over CAR cell expression (e.g. WO2014127261A1) due to small molecule-dependent heterodimerizing domains in each polypeptide of the CAR.

The cytoplasmic signaling domain (the intracellular signaling domain or the activating endodomain) of the CAR is responsible for activation of at least one of the normal effector functions of the immune cell in which the CAR is expressed, if the respective CAR is an activating CAR (normally, a CAR as described herein refers to an activating CAR, otherwise it is indicated explicitly as an inhibitory CAR (iCAR)). "Effector function" means a specialized function of a cell, e.g. in a T cell an effector function may be cytolytic activity or helper activity including the secretion of cytokines. The intracellular signaling domain refers to the part of a protein which transduces the effector function signal and directs the cell expressing the CAR to perform a specialized function. The intracellular signaling domain may include any complete, mutated or truncated part of the intracellular signaling domain of a given protein sufficient to transduce a signal which initiates or blocks immune cell effector functions.

Prominent examples of intracellular signaling domains for use in the CARs include the cytoplasmic signaling sequences of the T cell receptor (TCR) and co-receptors that initiate signal transduction following antigen receptor engagement.

Generally, T cell activation can be mediated by two distinct classes of cytoplasmic signaling sequences, firstly those that initiate antigen-dependent primary activation through the TCR (primary cytoplasmic signaling sequences, primary cytoplasmic signaling domain) and secondly those that act in an antigen-independent manner to provide a secondary or co-stimulatory signal (secondary cytoplasmic signaling sequences, co-stimulatory signaling domain). Therefore, an intracellular signaling domain of a CAR may comprise one or more primary cytoplasmic signaling domains and/or one or more secondary cytoplasmic signaling domains.

Primary cytoplasmic signaling domains that act in a stimulatory manner may contain ITAMs (immunoreceptor tyrosine-based activation motifs).

Examples of ITAM containing primary cytoplasmic signaling domains often used in CARs are that those derived from TCRζ (CD3ζ), FcRgamma, FcRbeta, CD3gamma, CD3delta, CD3epsilon, CD5, CD22, CD79a, CD79b, and CD66d. Most prominent is sequence derived from CD3ζ.

The cytoplasmic domain of the CAR may be designed to comprise the CD3 ζ signaling domain by itself or combined with any other desired cytoplasmic domain(s). The cytoplasmic domain of the CAR can comprise a CD3 ζ chain portion and a co-stimulatory signaling region (domain). The co-stimulatory signaling region refers to a part of the CAR comprising the intracellular domain of a co-stimulatory molecule. A co-stimulatory molecule is a cell surface molecule other than an antigen receptor or their ligands that is required for an efficient response of lymphocytes to an antigen. Examples for a co-stimulatory molecule are CD27, CD28, 4-1BB (CD137), OX40, CD30, CD40, PD-1, ICOS, lymphocyte function-associated antigen-1 (LFA-1), CD2, CD7, LIGHT, NKG2C, B7-H3.

The cytoplasmic signaling sequences within the cytoplasmic signaling part of the CAR may be linked to each other with or without a linker in a random or specified order. A short oligo- or polypeptide linker, which is preferably between 2 and 10 amino acids in length, may form the linkage. A prominent linker is the glycine-serine doublet.

As an example, the cytoplasmic domain may comprise the signaling domain of CD3ζ and the signaling domain of CD28. In another example the cytoplasmic domain may comprise the signaling domain of CD3ζ and the signaling domain of CD137. In a further example, the cytoplasmic domain may comprise the signaling domain of CD3ζ, the signaling domain of CD28, and the signaling domain of CD137.

As aforementioned either the extracellular part or the transmembrane domain or the cytoplasmic domain of a CAR may also comprise a heterodimerizing domain for the aim of splitting key signaling and antigen recognition modules of the CAR.

The CAR may be further modified to include on the level of the nucleic acid encoding the CAR one or more operative elements to eliminate CAR expressing immune cells by virtue of a suicide switch. The suicide switch can include, for example, an apoptosis inducing signaling cascade or a drug that induces cell death. In one embodiment, the nucleic acid expressing and encoding the CAR can be further modified to express an enzyme such thymidine kinase (TK) or cytosine deaminase (CD). The CAR may also be part of a gene expression system that allows controlled expression of the CAR in the immune cell. Such a gene expression system may be an inducible gene expression system and wherein when an induction agent is administered to a cell being transduced with said inducible gene expression system, the gene expression system is induced and said CAR is expressed on the surface of said transduced cell.

In some embodiments, the endodomain may contain a primary cytoplasmic signaling domains or a co-stimulatory region, but not both.

In some embodiment of the invention the CAR may be a "SUPRA" (split, universal, and programmable) CAR, where a "zipCAR" domain may link an intra-cellular costimulatory domain and an extracellular leucine zipper (WO2017/091546). This zipper may be targeted with a complementary zipper fused e.g. to an scFv region to render the SUPRA CAR T cell tumor specific. This approach would be particularly useful for generating universal CAR T cells for various tumors;

adapter molecules could be designed for tumor specificity and would provide options for altering specificity post-adoptive transfer, key for situations of selection pressure and antigen escape.

If the CAR is an inhibitory CAR (referred to herein normally as "iCAR"), then said CAR may have the same extracellular and/or transmembrane domains as the activating CAR but differs from the activating CAR with regard to the endodmain.

The at least one endodomain of the inhibitory CAR may be a cytoplasmic signaling domain comprising at least one signal transduction element that inhibits an immune cell or comprising at least one element that induces apoptosis.

Inhibitory endodomains of an iCAR are well-known in the art and have been described e.g. in WO2015075469A1, WO2015075470A1, WO2015142314A1, WO2016055551A1, WO2016097231A1, WO2016193696A1, WO2017058753A1, WO2017068361A1, WO2018061012A1, and WO2019162695A1.

Said at least one signal transduction element that inhibits or may be capable of inhibiting an (effector) immune cell of said iCAR may be a signal transduction element of an immune checkpoint protein.

Figure 4:
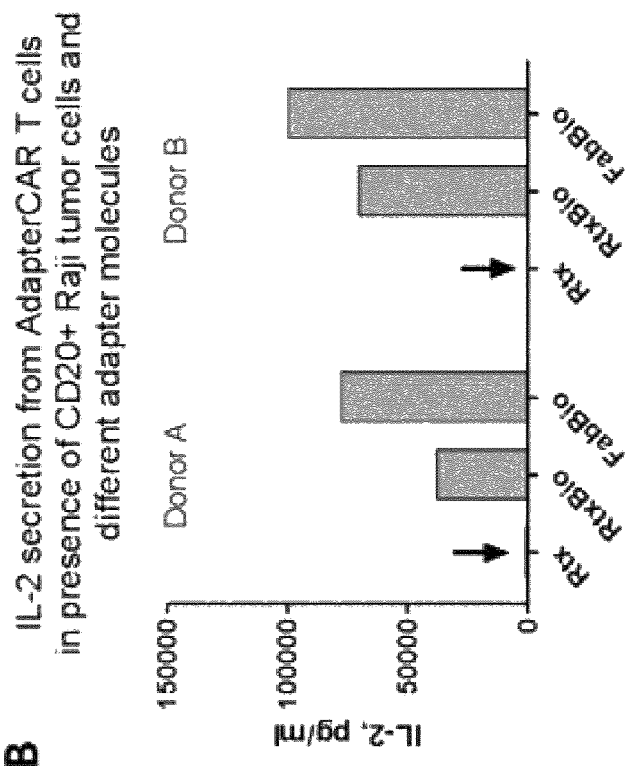
FIGS. 4A and 4B show that use of monobiotinylated Fabs can increase target cell specific cytokine release from adapter CAR T cells. Cytokine secretion after 18 h of anti-biotin CAR T cells (25.000 cells) in co-culture with (FIG. 4A) Mel526 tumor cells expressing CD20 and (FIG. 4B) Raji tumor cells, at an effector to target cell ratio of 1:1. Unlabeled Rituximab (Rtx), Rituximab-Biotin (RtxBio) and monobiotinylated Fab (FabBio) were added to the co-culture at $2\times10^{-11}$ mol/l. On both tumor cell lines, use of the monobiotinylated Fab shows increased cytokine secretion from CAR T cells compare to the biotinylated antibody (Detection limit: 100000 µg/ml).
Figure 4:
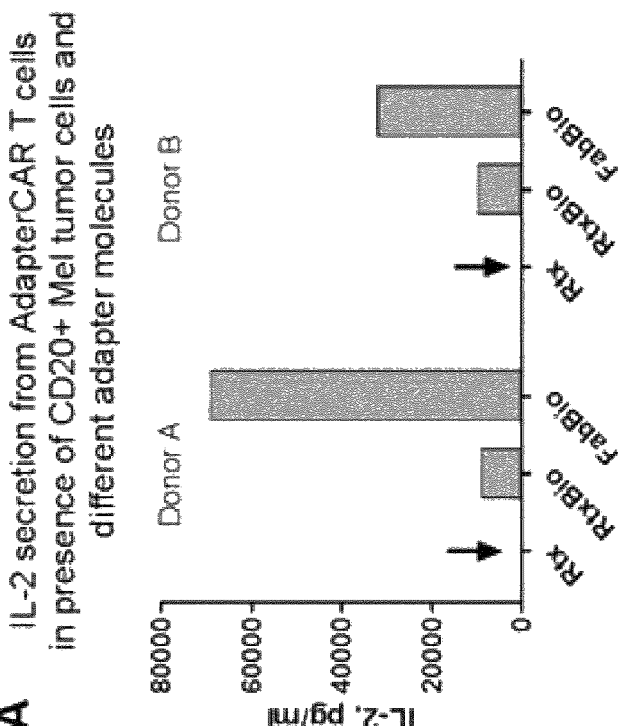

Said inhibitory signal transduction element may be selected from the groups consisting of:

the immunoglobulin superfamily (IgSF) and tumour necrosis factor receptor superfamily (TNFRSF) including immune checkpoint proteins CD22, CD31, CD33, CD47, CD85A (LIR3), CD85C (LIR8), CD85D (LIR2), CD87J (LIR1), CD85K (LIR5), CD89 (B71), CD94 (KLRD1), CD152 (CTLA4), CD158A (KIR2DL1), CD158B1 (KIR2DL2), CD158B2 (KIR2DL3), CD158D (KIR2DL4), CD158E1 (KIR3DL1), CD158F (KIR2DL5A) CD158K (KIR3DL2), CD158Z (KIR3DL3), CD159a, CD159c, CD160, CD223 (LAG3), CD244 (SLAMF4), CD272 (BTLA), CD274 (PDL1), CD279 (PD1), CD328 (Siglec7), CD329 (Siglec9), CD352 (SLAMF6), CEACAM1, CEACAM2, FcgammaR, G6b-B, KIR2DL5B, KLRG1, LAIR1, PD1H (Vista), PIR-B, Siglec2, Siglec3, Siglec5, Siglec6, Siglec8, Siglec10, Siglec11, Siglec12, TIGIT, TIM2, TIM3, and TLT-1 protein tyrosine phosphatases ACP1, CDC14A, CDC14B, CDC14C, CDC25A, CDC25B, CDC25C, CDKN3, DNAJC6, DUPD1, DUSP1, DUSP10, DUSP11, DUSP12, DUSP13, DUSP14, DUSP15, DUSP16, DUSP18, DUSP19, DUSP2, DUSP21, DUSP22, DUSP23, DUSP26, DUSP27, DUSP28, DUSP3, DUSP4, DUSP5, DUSP6, DUSP7, DUSP8, DUSP9, EPM2A, FIG4, GAK, INPP5A, INPP5B, INPP5D, INPP5E, INPP5F, INPP5J, INPP5K, INPPL1, MTM1, MTMR1, MTMR10, MTMR11, MTMR12, MTMR14, MTMR2, MTMR3, MTMR4, MTMR6, MTMR7, MTMR8, MTMR9, OCRL, PALD1, PIP4P1, PIP4P2, PTEN, PTP4A1, PTP4A2, PTP4A3, PTPDC1, PTPMT1, PTPN1, PTPN11, PTPN12, PTPN13, PTPN14, PTPN18, PTPN2, PTPN20, PTPN21, PTPN22, PTPN23, PTPN3, PTPN4, PTPN5, PTPN6, PTPN7, PTPN9, PTPRA, PTPRB, PTPRC, PTPRD, PTPRE, PTPRF, PTPRG, PTPRH, PTPRJ, PTPRK, PTPRM, PTPRN, PTPRN2, PTPRO, PTPRQ, PTPRR, PTPRS, PTPRT, PTPRU, PTPRZ1, RNGTT, SACM1L, SBFT, SBF2, SSH1, SSH2, SSH3, STYX, STYXL1, SYNJ1, SYNJ2, TNS1, TNS2, TNS3, TNS4, TPTE, and TPTE2.

Said at least one signal transduction element that inhibits an immune cell of said iCAR may be also selected from STimulator of INterteron Genes (STING); immunoreceptor tyrosine-based inhibitory motif (ITIM) containing proteins, immunoreceptor tyrosine-based switch motif (ITSM) containing proteins, T cell immunoglobulin and IITM domain (TIGIT), and adenosine receptor (e.g. A2aR).

Said at least one signal transduction element that inhibits an immune cell of said iCAR may be also a tyrosine phosphatase domain from a Src homolog (SH2) domain-containing protein tyrosine phosphatase which is recruited by a phosphorylated Immunoreceptor Tyrosine-based Activation motif (ITIM).

Said at least one signal transduction element that inhibits an immune cell of said iCAR may be also a tyrosine phosphatase domain from a Src homolog (SH2) domain-containing protein tyrosine phosphatase which is recruited by a phosphorylated Immunoreceptor Tyrosine-based Activation motif (ITIM).

Said at least one signal transduction element that inhibits an immune cell of said iCAR may be also (i) a truncated protein which comprises an SH2 domain from a protein which binds a phosphorylated immunoreceptor tyrosine-based activation motif (ITAM), but lacks a kinase domain; or (ii) a truncated protein which comprises an SH2 domain from a protein which binds a phosphorylated immunoreceptor tyrosine-based inhibition motif (ITIM) but lacks a phosphatase domain; or (iii) a fusion protein which comprises (a) an SH2 domain from a protein which binds a phosphorylated immunoreceptor tyrosine-based activation motif (ITAM) or from a protein which binds a phosphorylated immunoreceptor tyrosine-based inhibition motif (ITIM); and (ii) a heterologous domain. Said heterologous domain may be a phosphatase domain or a kinase domain. Said at least one element that induces apoptosis may be e.g. a Tumor-necrosis-factor related apoptosis inducing ligand (TRAIL) receptor or a CD200 receptor as described e.g. in detail in WO20160972331A1.

The CARs of the present invention may be designed to comprise any portion or part of the above-mentioned domains as described herein in any order and/or combination resulting in a functional CAR, i.e. a CAR that mediated an immune effector response of the immune effector cell that expresses the CAR as disclosed herein or that has an inhibitory function (iCAR) as disclosed herein.

The term "tagged polypeptide" as used herein refers to a polypeptide that has bound thereto directly or indirectly at least one additional component, i.e. the tag. The tagged polypeptide as used herein is able to bind an antigen expressed on a target cell. The polypeptide may be an antibody or antigen binding fragment thereof that binds to an antigen expressed on the surface of a target cell such as a (hematopoietic) stem cell, or a tumor associated antigen on a cancer cell. The polypeptide of the tagged polypeptide alternatively may a cytokine or a growth factor or another soluble polypeptide that is capable of binding to an antigen of a target cell.

The terms "adapter" or "adapter molecule" or "tagged polypeptide" as used herein may be used interchangeably.

The tag may be e.g. a hapten or dextran and the hapten or dextran may be bound by the antigen binding domain of the polypeptide, e.g. a CAR, comprising an antigen binding domain specific for the tag.

Haptens such as e.g. FITC, biotin, PE, streptavidin or dextran are small molecules that elicit an immune response only when attached to a large carrier such as a protein; the carrier may be one that also does not elicit an immune response by itself. Once the body has generated antibodies to a hapten-carrier adduct, the small-molecule hapten may also be able to bind to the antibody, but it will usually not initiate an immune response; usually only the hapten-carrier adduct can do this.

But the tag may also be a peptide sequence e.g. chemically or recombinantly coupled to the polypeptide part of the tagged polypeptide. The peptide may be selected from the group consisting of c-Myc-tag, Strep-Tag, Flag-Tag, and Polyhistidine-tag. The tag may also be streptavidin. The tag portion of the tagged polypeptide is only constrained by being a molecular that can be recognized and specifically bound by the antigen binding domain specific for the tag of the CAR. For example, when the tag is FITC (Fluorescein isothiocyanate), the tag-binding domain may constitute an anti-FITC scFv. Alternatively, when the tag is biotin or PE (phycoerythrin), the tag-binding domain may constitute an anti-biotin scFv or an anti-PE scFv.

The term "antibody" as used herein is used in the broadest sense to cover the various forms of antibody structures including but not being limited to monoclonal and polyclonal antibodies (including full length antibodies), multi-specific antibodies (e.g. bispecific antibodies), antibody fragments, i.e. antigen binding fragments of an antibody, immunoadhesins and antibody-immunoadhesin chimeras, that specifically recognize (i.e. bind) an antigen. "Antigen binding fragments" comprise a portion of a full-length antibody, preferably the variable domain thereof, or at least the antigen binding site thereof ("an antigen binding fragment of an antibody"). Examples of antigen binding fragments include Fab (fragment antigen binding), scFv (single chain fragment variable), single domain antibodies, diabodies, dsFv, Fab', diabodies, single-chain antibody molecules, and multispecific antibodies formed from antibody fragments.

The terms "having specificity for", "specifically binds" or "specific for" with respect to an antigen-binding domain of an antibody, of a fragment thereof or of a CAR refer to an antigen-binding domain which recognizes and binds to a specific antigen, but does not substantially recognize or bind other molecules in a sample. An antigen-binding domain that binds specifically to an antigen from one species may bind also to that antigen from another species. This cross-species reactivity is not contrary to the definition of that antigen-binding domain as specific. An antigen-binding domain that specifically binds to an antigen may bind also to different allelic forms of the antigen (allelic variants, splice variants, isoforms etc.). This cross reactivity is not contrary to the definition of that antigen-binding domain as specific.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are several subsets of T cells, each with a distinct function.

T helper cells (TH cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including TH1, TH2, TH3, TH17, Th9, or TFH, which secrete different cytokines to facilitate a different type of immune response. Signaling from the APC directs T cells into particular subtypes.

Cytotoxic T cells (TC cells, or CTLs) destroy virally infected cells and tumor cells, and are also implicated in transplant rejection. These cells are also known as CD8+ T cells since they express the CD8 glycoprotein at their surface. These cells recognize their targets by binding to antigen associated with MHC class I molecules, which are present on the surface of all nucleated cells.

The term "cytotoxic immune effector cells" as used herein refers to relatively short-lived activated cells that defend the body in an immune response. Effector B cells are called plasma cells and secrete antibodies, and activated T cells include cytotoxic T cells and helper T cells, which carry out cell-mediated responses. The Effector T cell describes a group of cells that includes several T cell types that actively respond to a stimulus, such as co-stimulation. It includes CD4+, CD8+, Treg cells.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—Foxp3+ Treg cells and Foxp3− Treg cells.

Natural killer T cells (NKT cells—not to be confused with natural killer cells of the innate immune system) bridge the adaptive immune system with the innate immune system. Unlike conventional T cells that recognize peptide antigens presented by major histocompatibility complex (MHC) molecules, NKT cells recognize glycolipid antigen presented by a molecule called CD1d. Once activated, these cells can perform functions ascribed to both Th and Tc cells (i.e., cytokine production and release of cytolytic/cell killing molecules).

The term "natural killer cells (NK cells)" are defined as large granular lymphocytes (LGL) and constitute the third kind of cells differentiated from the common lymphoid progenitor-generating B and T lymphocytes. NK cells are known to differentiate and mature in the bone marrow, lymph nodes, spleen, tonsils, and thymus, where they then enter into the circulation. NK cells differ from natural killer T cells (NKTs) phenotypically, by origin and by respective effector functions; often, NKT cell activity promotes NK cell activity by secreting IFNγ. In contrast to NKT cells, NK cells do not express T-cell antigen receptors (TCR) or pan T marker CD3 or surface immunoglobulins (Ig) B cell receptors, but they usually express the surface markers CD16 (FcγRIII) and CD56 in humans, NK1.1 or NK1.2 in C57BL/6 mice. Up to 80% of human NK cells also express CD8. Continuously growing NK cell lines can be established from cancer patients and common NK cell lines are for instance NK-92, NKL and YTS.

The terms "immune cell" or "immune effector cell" may be used interchangeably and refer to a cell that may be part of the immune system and executes a particular effector function such as alpha-beta T cells, NK cells, NKT cells, B cells, innate lymphoid cells (ILC), cytokine induced killer (CIK) cells, lymphokine activated killer (LAK) cells, gamma-delta T cells, monocytes or macrophages. Preferentially these immune cells are human immune cells. Preferred immune cells are cells with cytotoxic effector function such as alpha-beta T cells, NK cells, NKT cells, ILC, CIK cells, LAK cells or gamma-delta T cells. Most preferred immune effector cells are T cells and NK cells. "Effector function" means a specialized function of a cell, e.g. in a T cell an effector function may be cytolytic activity or helper activity including the secretion of cytokines.

The term "accessory cells" as used herein refers to blood cells that are CD14, CD11b, CD11c, CD123, CD33, CD36, CD47, CD66b, CD235a, CD146 and/or CD326 expressing cells or combinations thereof The term "contributory cells" as used herein refers to blood cells that are CD14, CD11b, CD11c, CD123, CD33, CD36, CD47, CD66b, CD235a, CD146 and CD326 expressing cells or combinations thereof.

The terms "accessory cells" and "contributory cells" may be used interchangeably.

CD34+ hematopoietic stem cells are cells that have the capacity to self-renew and simultaneously give rise to hemopoietic cells of all lineages, such as erythrocytes, T and B lymphocytes, natural killer (NK) cells, granulocytes, monocytes, platelets, dendritic cells and other cells of the blood and are used to replenish the blood cells during the lifetime of an individual. CD34+ hematopoietic stem cells may also comprise one or more of the following antigens: CD33+, and/or CD38+, and/or CD45RA+, and/or CD71+, and/or CD90+, and/or CD131+, and/or CD133+, and/or CD135+. In some embodiments of the invention, the hematopoietic stem cells may be CD34+, CD45RAnegative, CD38negative and CD90+.

The "bone marrow" is an organ composed of hematopoietic cells, marrow adipose tissue, and supportive stromal cells. In adult humans, bone marrow is primarily located in the ribs, vertebrae, sternum, and bones of the pelvis and serves as the major organ that generates all the cells of the blood.

The term "bone marrow's stromal cells" means all supportive cells that are located in the bone marrow niche and are used to support i.e. maintain the homeostasis of all blood cells. These are usually, but not restricted, adherent cells and in close proximity to other cells of the blood, including hemopoietic stem cells.

The term "genetically engineered CD34+ hematopoietic stem cells are cells that have been corrected with regard to a disease" as used herein means they have been processed in a way to either acquire a gene previously missing or mutated (gene addition) or to express another gene which is considered therapeutic. In the case of thalassemia and sickle cell disease this could mean that the CD34+ hemopoietic stem cells are processed in such a way, i.e. via electroporation, to express down regulators of known repressors of fetal hemoglobin so as to prevent silencing of fetal hemoglobin.

A single-gene (or monogenic) disorder/disease is the result of a single mutated gene. Over 6000 human diseases are caused by single-gene defects. Single-gene disorders can be passed on to subsequent generations in several ways.

As used herein, the term "antigen" is intended to include substances that bind to or evoke the production of one or more antibodies and may comprise, but is not limited to, proteins, peptides, polypeptides, oligopeptides, lipids, carbohydrates such as dextran, haptens and combinations thereof, for example a glycosylated protein or a glycolipid. The term "antigen" as used herein refers to a molecular entity that may be expressed on the surface of a target cell and that can be recognized by means of the adaptive immune system including but not restricted to antibodies or TCRs, or engineered molecules including but not restricted to endogenous or transgenic TCRs, CARs, scFvs or multimers thereof, Fab-fragments or multimers thereof, antibodies or multimers thereof, single chain antibodies or multimers thereof, or any other molecule that can execute binding to a structure with high affinity.

The term "marker" as used herein refers to an antigen that is specifically expressed by a certain cell type. Preferentially, the marker is a cell surface marker, The terms "marker" and "antigen" as used herein may be used interchangeably.

The term "target cell" as used herein refers to cell which expresses an antigen on its cell surface that should be recognized (bound) by the antigen binding domain of the CAR as disclosed herein or by the antigen binding domain of the tag of the tagged polypeptide as disclosed herein.

Immunotherapy is a medical term defined as the "treatment of disease by inducing, enhancing, or suppressing an immune response" Immunotherapies designed to elicit or amplify an immune response are classified as activation immunotherapies, while immunotherapies that reduce or suppress are classified as suppression immunotherapies. Cancer immunotherapy as an activating immunotherapy attempts to stimulate the immune system to reject and destroy tumors. Adoptive cell transfer uses cell-based, preferentially T cell-based or NK cell-based cytotoxic responses to attack cancer cells. T cells that have a natural or genetically engineered reactivity to a patient's cancer are generated in-vitro and then transferred back into the cancer patient. Then the immunotherapy is referred to as "CAR immunotherapy" or in case of use of T cells only as "CAR T cell therapy" or "CAR T cell immunotherapy".

The term "treatment" as used herein means to reduce the frequency or severity of at least one sign or symptom of a disease.

The terms "therapeutically effective amount" or "therapeutically effective population" mean an amount of a cell population which provides a therapeutic benefit in a subject.

As used herein, the term "subject" refers to an animal. Preferentially, the subject is a mammal such as mouse, rat, cow, pig, goat, chicken dog, monkey or human More preferentially, the subject is a human. The subject may be a subject suffering from a disease as disclosed herein.

The term "autologous" as used herein refers to any material derived from the same subject to who it is later re-introduced.

The term "allogeneic" as used herein refers to any material derived from a different subject of the same species as the subject to who the material is re-introduced.

The term "expression" as used herein is defined as the transcription and/or translation of a particular nucleotide sequence driven by its promoter in a cell.

The terms "engineered cell" and "genetically modified cell" as used herein can be used interchangeably. The terms mean containing and/or expressing a foreign gene or nucleic acid sequence which in turn modifies the genotype or phenotype of the cell or its progeny. Especially, the terms refer to the fact that cells, preferentially T cells can be manipulated by recombinant methods well known in the art to express stably or transiently peptides or proteins which are not expressed in these cells in the natural state. For example, T cells, preferentially human T cells are engineered to express an artificial construct such as a chimeric antigen receptor on their cell surface.

The cluster of differentiation (abbreviated as CD) is a protocol used for the identification and investigation of cell surface molecules, regularly polypeptides, providing targets for immunophenotyping of cells.

The term "combination of compositions" as used herein refers to two or more compositions that may be used together (combined) either directly or one after another to exert the desired a effect as disclosed herein. Alternatively, the terms "system" or "kit" may be used instead of "combination of compositions".

The term engraftment means the process during which hemopoietic stem cells, from an autologous or allogeneic donor after infusion into the body of a recipient, can reach the bone marrow of the recipient, can be successfully implanted in the bone marrow of the recipient and subsequently give rise to all cell lineages of blood cells such as such as erythrocytes, T and B lymphocytes, natural killer (NK) cells, granulocytes, monocytes, platelets, dendritic cells and all other cells of the blood and can replenish the blood cells during the rest of the lifetime of the recipient.

EXAMPLES

Example #1. Functionality of the Biotin-Crosslinker Y Conjugated to the Antigen Recognition Moiety Z (CD20 Fab) Binding to CD20 Antigen on CD20 Positive Jeko 1 Cells and Staining with Fluorescent Anti-Biotin APC CD20 positive Jeko-1 cells were seeded in a 96-well plate (50.000 cells/well) and incubated for 10 min at 4° C. with biotin-crosslinker conjugated anti-CD20 FAb (Rtx Fab MS2) at different concentrations (0.01-100 μg/ml and 0 μg/ml as negative control) in a total volume of 50 μl Buffer A (CliniMACS PBS/EDTA Buffer+0.5% BSA). After that 50 μl of anti-Biotin APC (1:50 in Buffer A, Miltenyi Biotec, Art. No. 130-110-952) was added, and the sample was further incubated at 4° C. for additional 10 min. As positive control anti-human CD20 APC conjugate was used to stain a control sample according to the manufacturer's protocol (Miltenyi Biotec, Art. No. 130-111-525). Finally, 100 μl of Buffer A was added to each sample and data was acquired at the MACSQuant Analyzer 10 (Miltenyi Biotec 130-096-343). Frequency of CD20+ cells (gated on only aBio APC as negative control) and median fluorescence intensity of positive cells was analysed (FIG. 1 below). Fluorescence and thereby biotinylated FAb bound to target cells was detected at concentration as low as 0.1 μg/ml and median fluorescence intensity increased up to a concentration of 100 μg/ml, indicating that free CD20 binding sites are still available at concentrations of 10 μg/ml, under the conditions used.

Example #2. Functionality of Killing Target Cancer Cells by Combination of X-Y-Z Units PBMCs were isolated from buffy coat of healthy donors by separation on Ficoll. T cells were selected from PBMCs by MACS technology using the Pan T cell isolation kit (Miltenyi Biotec, 130-096-535). For T cell activation and -expansion the T cells were seeded at $1 \times 10^6$ cells/mL in TexMACS medium containing IL-7 (10 ng/mL) and IL-15 (10 ng/mL) and 1% (v/v) T Cell TransAct, human (Miltenyi Biotec, Art No: 130-111-160) and incubated at 37° C., 5% $CO_2$. Transduction was performed on day 1 after activation. For this, LV supernatant encoding for adapter CARs was added to T cells at a MOI of 5 and cells were carefully resuspended by pipetting up and down. TransAct was removed on day 3 and T cells were further expanded maintaining a cell density of $2 \times 10^6$ cells/mL. On day 6 LNGFR-expressing cells were separated by MACS using anti-LNGFR microbeads on an LS column (Miltenyi Biotec) according to the manufacturer's instructions. Selected, LNGFR+ cells were further expanded up to day 12 and then frozen in aliquots at $1 \times 10^7$ cells/ml in TexMACS+20% (v/v) FCS+10% (v/v) DMSO and stored in liquid nitrogen. Aliquots of cells were thawed and cells were washed and recovered in TexMACS containing IL-7 (10 ng/mL) and IL-15 (10 ng/mL) for 48 h before the experiment.

Figure 2:
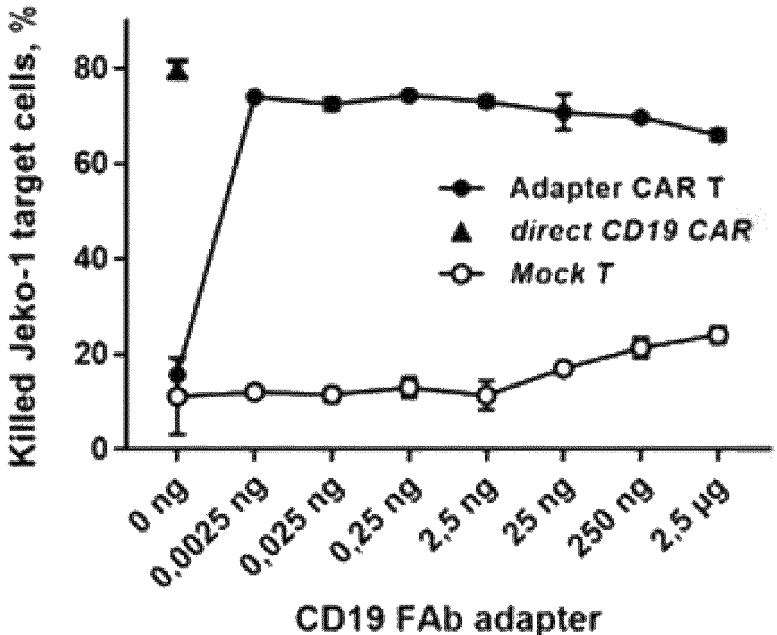
FIG. 2. Proof-of-concept showing the specific killing of target cancer cells (Jeko-1 cells) expressing an antigen recognized by the X-Y-Z construct comprised of: Anti-Biotin CAR T cells (X), biotin-CD19Fab (Y-Z). The Y-Z complex was added in increasing amounts (0-2.5 µg) to 10000 Jeko cells and 50000 CAR T cells (closed circles). Positive control (filled triangle) or negative control Mock (UTD) cells (open circles).

Immediately before the experiment GFP transduced Jeko-1 target cells were resuspended in TexMACS without cytokines and 10.000 cells were added to each well of a 96-well plate. Then CAR transduced, and untransduced (Mock) T cells were resuspended in TexMACS without cytokines and 50.000 cells were added to the respective wells of a 96-well plate. Subsequently, crosslinked and biotinylated CD19 Fab was added to each well at the indicated concentrations and the sample (V=200 μl) containing Jeko-1 target cells, T cells and Fab, was mixed by carefully pipetting up and down. As a positive control direct anti-CD19 CAR T cells (50.000) were co-incubated with 10.000 target cells without addition of Fab. All samples were incubated at 37° C., 5% $CO_2$ for 16 h. Killing was quantified on a MACSQuant flow cytometer. Propidium iodide was added to the cells immediately before the assay. Killing was evaluated by counting GFP positive and viable (propidium iodide negative) target cells and is expressed as [Killing, %]=[viable GFP$^+$ target cells in untreated sample]/[viable GFP+ target cells in treated sample]×100% (FIG. 2). Upon titration of the Fab molecule the Direct CD19 CAR killing after 16 h is in the range of 80%. In case of the adapter CAR, maximal killing (75%) is already observed at adapter doses as low as 0.0025 ng in a sample of 200 μl (0.0125 ng/ml) and decreased only by approx. 5% over 6 decades of increasing different adapter concentrations. Furthermore, adapter associated background killing activity with Mock T cells is not detected up to 2.5 ng adapter added in the 200 μl sample (12.5 ng/ml). Overall this indicates that the Fab-based adapter in combination with the adapter CAR T cells enables a high degree of specific lysis (65%) over a broad concentration range covering over 4 decades of adapter concentrations.

Figure 3:
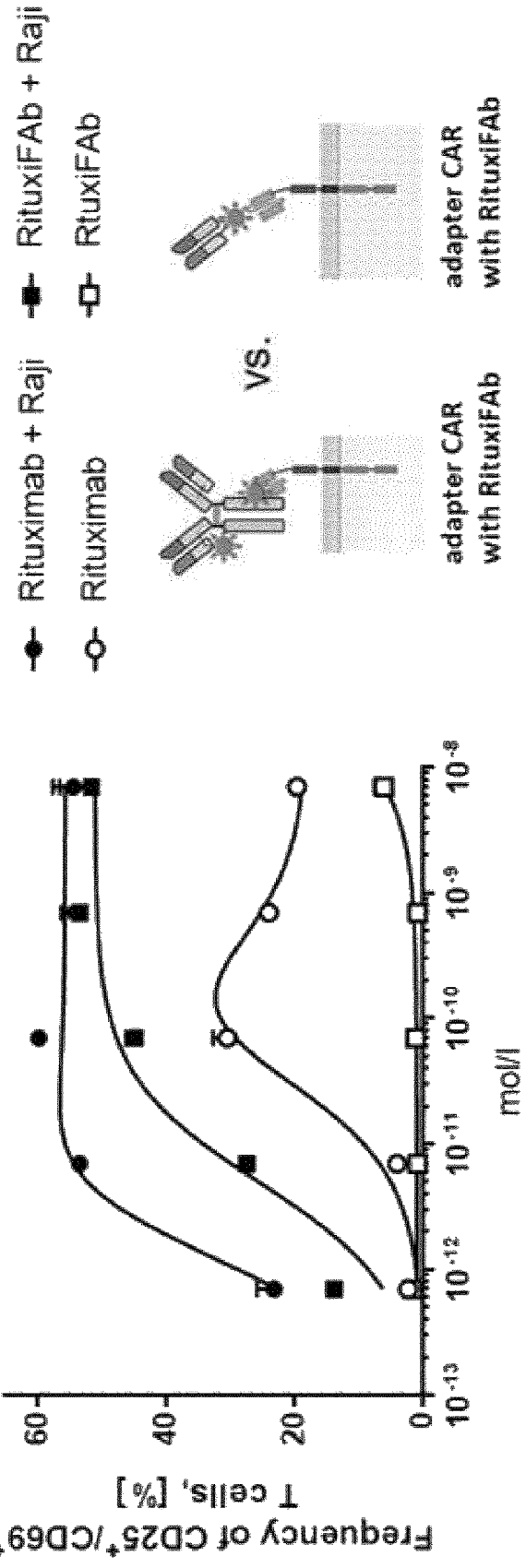
FIG. 3. Monobiotinylated Fabs induce activation of adapter CAR T cells only in presence of target cells, while adapter molecules based on full length antibodies, and with multiple affinity units, can induce activation of CAR T cells also in absence of target cells. Co-culture (24 h) of adapter CAR T and Raji target cells at an effector to target cell ratio of 1. Antibody (Rituximab) or Fab (RituxiFab) is added at different concentrations (as indicated). The frequency of activated cells (defined by expression of CD69+ and CD25+) is shown.

Example #3. Unspecific Activation of CAR T-Cells Using Biotinilated Ab Vs Mono-Biotinilated Fab Expression of markers CD25 and CD69 is correlated with activation of T cells, which in turn is related to their cytotoxic effector functions. In order to monitor T cell activation, adapter CAR T cells were incubated for 24 h at 37° C. and 5% $CO_2$ at increasing concentrations of adapter molecule in presence (closed symbols, E:T=1:1) or absence (open symbols) of target cells. Two different types of adapter molecule were evaluated: i) Rituximab (anti-CD20 antibody) which was conjugated by NHS-esters and has on average 2-3 Biotin affinity units and the ii) Fab fragment which has 1 Biotin affinity unit/molecule. Activation of T cells was analysed on a MACSQuant flow cytometer and the fraction of activated cells was defined by the fraction of CD69+ and CD25+ cells Importantly both adapters efficiently triggered activation of adapter CAR T cells in the presence of target cells in a concentration range of $1\times10^{-10}$-$1\times10^{-8}$ mol/l adapter (50% activation, depending on E:T ratio). However, in absence of target cells only the antibody was able to induce activation of the T cells (maximum activation was observed at a concentration of $1\times10^{-10}$ mol/l), while monobiotinylated Fab was not able to induce activation of T cells in absence of target cells up to a concentration of $1\times10^{-9}$ mol/l (FIG. 3).

Activation of CAR T cells in general should be strictly dependent on presence of target cells and cognate adapter molecules, thereby increasing the safety of the approach, activation of T cells in absence of adapter molecules therefore is an undesired property of the adapter which is observed with the whole antibody molecule but not with the monobiotinylated Fab. Use of monobiotinylated Fab as adapter molecule might therefore improve overall safety of the adapter CAR technology.

Example #4. Monobiotinylated Fab Shows Increased Cytokine Secretion from CAR T Cells Compare to the Biotinylated Antibody Use of monobiotinylated Fab molecules can induce efficient release of proinflammatory cytokine (IL-2) from T cells. Different target cells Mel526 (CD20+) and Raji (CD20+) were cocultured in a 96-well plate with adapter CAR T cells at an E:T ratio of 1:1 in 200 μl. Adapter molecules Rituximab-Biotin (n=2-3 Biotin/molecule) and monobiotinylated Rituximab Fab were added at $2\times10^{-11}$ mol/l, as a negative control non-biotinylated Rituximab was used. After 18 h incubation at 37° C. and 5% $CO_2$ 100 μl supernatant was carefully removed from the culture and analysed using the MACSPlex Cytokine 12 Kit, human (Miltenyi Biotec Art. No. 130-099-169) according to the manufacturer's protocol. While in the samples containing only antibody no significant IL-2 release was observed, presence of biotinylated antibody triggered specific cytokine secretion on Mel526 and Raji cells (FIG. 4).

Notably in presence of the same concentration of biotinylated Fab, cytokine release was increased 3.2-7.4-fold on Mel526 cells and up to 2-fold on Raji cells compared to the biotinylated antibody. Overall this might be attributed to suboptimal orientations (multiple non-productive conformations) on the receptor, which are only possible for the whole antibody molecule having multiple affinity units. Thereby use of a monobiotinylated Fab may improve formation of productive conformations on the adapter CAR T cells in presence of target cells, allowing for an improved immunological synapse formation and cytokine release.

Example #5. Killing Assay Using Biotinilated Ab with Different DOL

Figure 5:
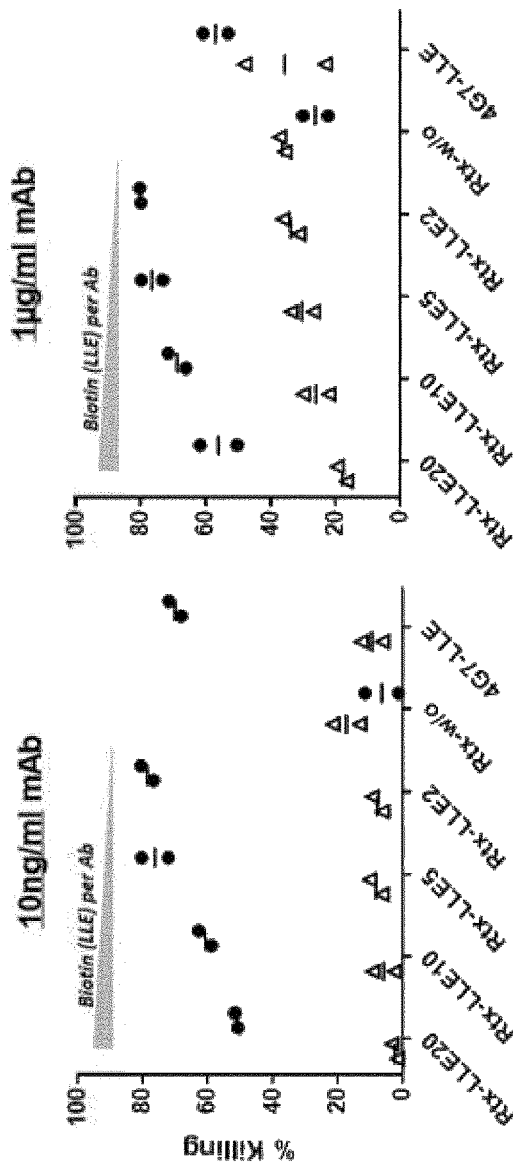
FIG. 5. A low degree of labeling improves adapter (Ab) functionality. CAR T effector cells (red) or Mock (untransduced, blue) T cells were co-cultured with Jeko-1 mantle cell lymphoma (E:T=5:1, 18 h), in presence of Rituximab-Biotin (anti-CD20 Ab) with different degrees of labeling (number of Biotins/Rituximab ranging from 0 (Rtx-LLE-w/o) up to 20 (Rtx-LLE20). As control an anti-CD19 antibody with 6 biotins/molecule was used. Different concentrations of mAb: 1 µg/ml and 10 ng/ml are shown. Maximal tumor cell lysis after 18 h is observed with antibody having a low degree of labeling (average of 2 biotin moieties/Rituximab molecule).
Figure 5:
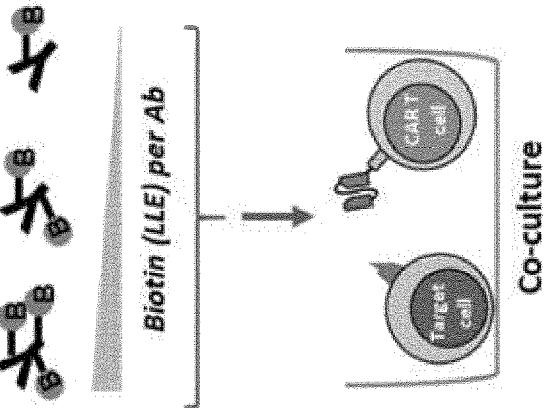

Functionality of adapter molecules having a variable number of affinity units was further addressed in an assay in which Rituximab was conjugated using different amounts of Biotin. The antibody modification by random labeling by succinimidyl-esters at amino groups was done according to protocols well known in the art. For modification, antibodies were rebuffered by passing over an Sephadex G25 column equilibrated in PEB buffer. Collected fractions were assayed for protein content using the Bradford assay. Protein containing fractions were pooled and the total volume determined Final protein concentration was measured by absorption at 280 nm Subsequently, the corresponding amount of Biotin-LC-LC-NHS (ThermoFisher Scientific, Mw 567.70 g/mol, Cat. No. 21343, CAS-No. 89889-52-1) was dissolved in DMSO. To obtain different degrees of labelling, different amounts of Biotin-LC-LC-NHS was added to reaction mix (3, 6, 12 and 25-fold molar excess). The antibody and DMSO/label mix was incubated at 30° C. for 1 h and then passed over a Sephadex G25 column. Again fractions were collected, assayed for protein concentration and protein containing fractions were pooled. Final protein concentration was measured by absorption at 280 nm Successful biotinylation was confirmed by LC-MS and by incubation of the antibodies on Jeko-1 cell line expressing the CD20 antibody target and secondary staining with a fluorochrome conjugated anti-biotin antibody, followed by FACS analysis. Rituximab conjugates having a degree of labelling form 2-3 up to 20 biotins/antibody were obtained and subsequently used as adapters used in a killing assay (FIG. 5).

While all biotinylated antibodies were able to mediate killing of target cells, maximum specific target cell lysis was observed with rituximab having a low degree of labelling, with 2-3 biotins per antibody. Notably, no lysines, representing the primary sites of modification for NHS esters can be found in the CDRs of Rituximab. Overall this may highlight importance of using a low degree of labelling on adapter molecules and highlight the importance of mono-functionalized adapters.

Example #6. Adapter CAR with CD20Fab-Biotin Reach the Bone Marrow of NSG Mice

Figure 6:
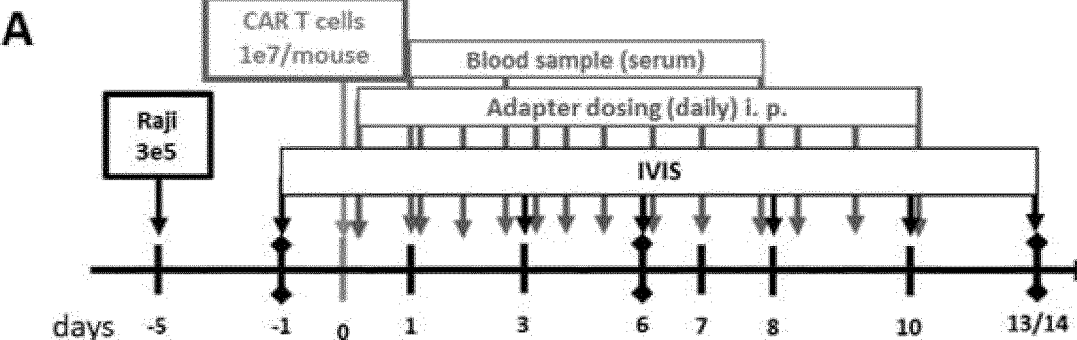
FIGS. 6A and 6B show functionality of anti-affinity unit CAR T cells in the presence of crosslinker-modified target cell binding domains (CD20Fab-Biotin) in vivo.
Figure 6:
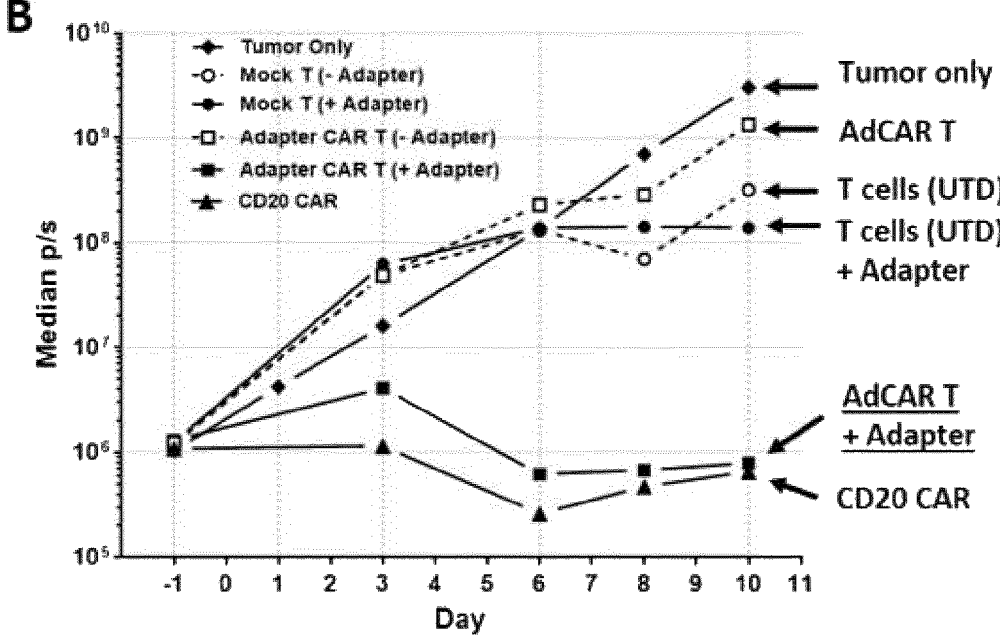

For the in vivo experiments NOD-SCID common γ chain−/− (NSG) mice of female sex were be used, age 7-10 weeks. These are severe combined immunodeficiency (SCID) mice derived on a non-obese diabetic (NOD) background with additional knockout of the common γ-chain (γc−/−). Mice were be obtained from external provider (Jackson labs) and kept in individually ventilated cages (IVC) at 5 animals per cage and group on a standard rodent diet (ssniff, Soest, Germany) Room temperature was constantly kept at 22° C. with an air humidity between 50-60%. Light-dark rhythm interval was 12 hours. General health status of all animals was monitored daily. Raji tumor cells, genetically modified to express firefly luciferase (ffLuc), were transferred by i.v. injection ($3 \times 10^5$ cells in 100 µl) and developed systemic leukaemia in the engrafted mice. Tumor progression was regularly monitored (total tumor burden/distribution) by bioluminescence imaging (BLI) in the IVIS (in vivo imaging system). After tumor engraftment for 5 days, adapter CAR T cells and CD20 CAR T cells were be dosed by i.v. injection ($1 \times 10^7$ cells per mouse, volume 100 µl) on day 0. Adapter molecules were administered daily by i.p. injection starting on the same day of tumor injection. Administration of adapter molecules was continued for 10 days and tumor progression was continuously monitored (FIG. 6).

While the untreated group which only received tumor cells, BLI was progressing from $1 \times 10^6$ on day 0 to up to $2 \times 10^9$ on day 10, CD20 CART cells were able to control tumor outgrowth efficiently with BLI signal of $7 \times 10^5$ on day 10. These results suggest, that the Adapter CAR T cells were able to reach the bone marrow and all other organs in the affected animals. Adapter CAR T cells in presence of adapter showed a very similar tumor control with median of $8 \times 10^5$ on day 10. In contrast Mock T cells in absence or presence of adapter and adapter CAR T cells in absence of adapter did not control tumor outgrowth, demonstrating that both adapter and adapter CAR T cells need to be present for an efficient tumor control in vivo. Furthermore this experiment highlights the functionality of the monobiotinylated CD20 Fab conjugate in a preclinical setting.

Example #7. Administration of Total Bone Marrow Cells in C57/BL6 Thalassemic Mice Treated with Busulfan Promotes Longer Engraftment Compared to Administration of Lin-Cells Under the Same Conditions We employed the established protocol utilizing busulfan as previously described (Ronen et al, 2011). Total bone marrow (BM) was flushed from femora and tibiae of 3-5-month old male or female donor β-thalassemic mice, injected intraperitonally with 150 mg/kg 5-fluorouracil (5FU), four days prior to BMT. For Lineage-negative (Lin-) cell selection, BM cells were subjected to lineage depletion by immunomagnetic separation using the Mouse BM Lineage Cell Depletion (Miltenyi Biotec). After magnetic separation, Lin-cells or total BM cells were pooled together from all mice and resuspended in StemSpan medium supplemented with the following cytokines: 50 ng/ml murine SCF, 50 ng/ml human IL-6, 25 ng/ml human TPO, 10 ng/ml murine IL-3, at a concentration of $1 \times 10^6$ cell/ml and incubated at 37° C. in a 5% $CO_2$-containing incubator for 30 hours. Following pre-stimulation, cells were harvested, washed twice in PBS containing 2% FBS and resuspended in PBS prior to BM transplantation. On the day of transplantation one million transduced total BM or 10.000 Lin-cells were injected by tail vein into recipients thalassemic mice or wt C57BL/6J, treated with 20 mgr/kg Busulfan for four subsequent days, starting four days before transplantation.

Figure 7:
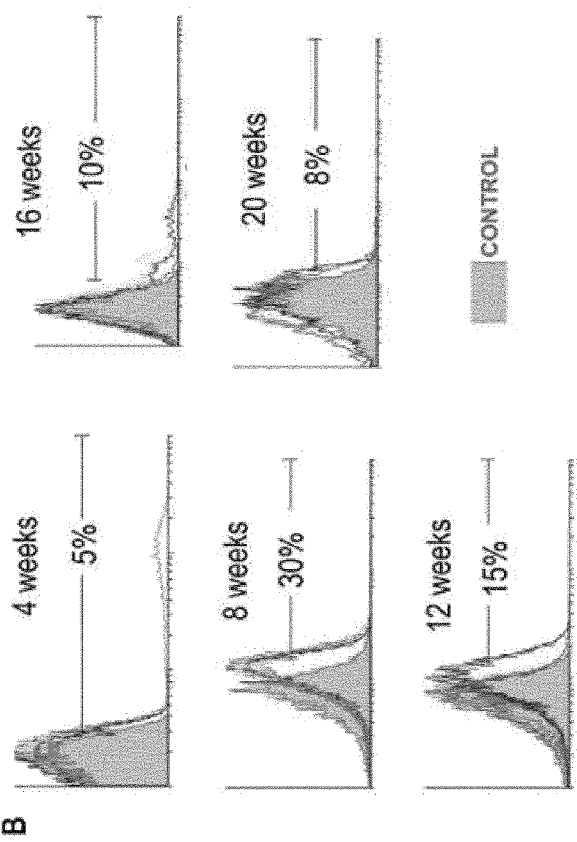
FIGS. 7A and 7B show engraftment of mice treated with Busulfan either by injection of Lin- cells (FIG. 7A) or total BM (FIG. 7B).
Figure 7:
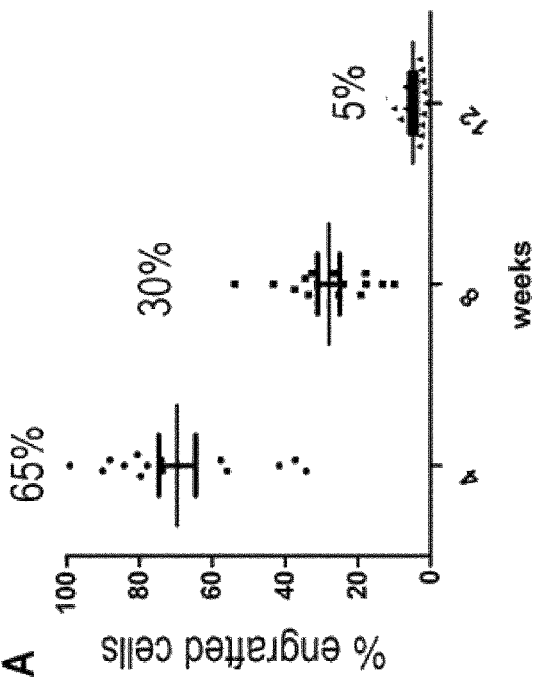

As shown in FIG. 7A, Lin-cells generated higher engraftment rates as within the first month that reached an average of 65%. However the mice within 8 weeks rapidly lost the engrafted cells, as by week 12, the average percentage of engrafted cells was lower than 10%. On the contrary, mice injected with the hemopoietic stem cells containing also the contributory cells (FIG. 7B) engrafted successfully, albeit at lower levels compared to mice that received only Lin-cells. This type of engraftment was generally sustained for a prolonged period of time, i.e. for 5 months (20 weeks). Mice engrafted with Lin-cells developed BM failure by 4 months, whereas, mice engrafted with total BM, developed BM failure after 6 months, indicating the survival advantage of the co-administration of the contributory cells.

The invention claimed is:

1. A method for eliminating hematopoietic stem cells in the bone marrow of a subject suffering from a hematologic malignancy or hemoglobinopathy and increasing engraftment efficiency of a population of CD34+ hematopoietic stem cells, the method comprising administering to said subject
 i) a composition comprising:
  (I) a population of T cells or NK cells comprising a chimeric antigen receptor specific for a tag of a tagged polypeptide, wherein said tagged polypeptide binds specifically to a hematopoietic stem cell antigen, and
  (II) said tagged polypeptide,
 thereby specifically eliminating said hematopoietic stem cells in the bone marrow of the subject and leaving unaffected the bone marrow's stromal cells, and
 ii) a composition comprising:
  a) a population of CD34+ hematopoietic stem cells, and
  b) an accessory cell population, wherein the accessory cell population is comprised of myeloid lineage cells that express at least one marker from the group consisting of CD14, CD11b, CD11c, CD123, CD33, CD36, CD47, CD66b, CD235a, CD146 and CD326,
 thereby increasing engraftment efficiency into the bone marrow of the subject.

2. The method according to claim 1, wherein said population of CD34+ hematopoietic stem cells are genetically engineered cells or healthy cells.

3. The method according to claim 1, wherein said accessory cell population comprises at least a population of CD14+ hematopoietic cells.

4. The method according to claim 1, wherein said hematopoietic stem cell antigen is c-Kit, CD34, CD33, CD71, CD90, CD131, CD133, or CD135.

5. The method according to claim 1, wherein the hemoglobinopathy is thalassemia or sickle cell disease.

\* \* \* \* \*